US011458463B2

(12) United States Patent
Khawaji et al.

(10) Patent No.: US 11,458,463 B2
(45) Date of Patent: Oct. 4, 2022

(54) CATALYST SYSTEMS

(71) Applicant: Saudi Arabian Oil Company, Dhahran (SA)

(72) Inventors: Motaz Khawaji, Thuwal (SA); Sohel Shaikh, Dhahran (SA); Wei Xu, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/537,677

(22) Filed: Nov. 30, 2021

(65) Prior Publication Data

US 2022/0168719 A1 Jun. 2, 2022

Related U.S. Application Data

(60) Provisional application No. 63/119,221, filed on Nov. 30, 2020, provisional application No. 63/119,136, filed on Nov. 30, 2020.

(51) Int. Cl.
*B01J 31/24* (2006.01)
*B01J 31/14* (2006.01)
*C07C 2/36* (2006.01)

(52) U.S. Cl.
CPC ......... *B01J 31/2409* (2013.01); *B01J 31/143* (2013.01); *C07C 2/36* (2013.01); *B01J 2231/20* (2013.01); *B01J 2531/62* (2013.01); *C07C 2531/14* (2013.01); *C07C 2531/24* (2013.01)

(58) Field of Classification Search
None
See application file for complete search history.

(56) References Cited

U.S. PATENT DOCUMENTS

| 2,738,151 | A | 3/1956 | Herzog |
| 3,061,602 | A | 10/1962 | Duck et al. |
| 3,686,350 | A | 8/1972 | Yamada et al. |
| 4,242,531 | A | 12/1980 | Carter |
| 4,484,016 | A | 11/1984 | Maschmeyer et al. |
| 4,528,415 | A | 7/1985 | Knudsen |
| 4,532,370 | A | 7/1985 | Le Quan et al. |
| 4,538,018 | A | 8/1985 | Carter |
| 4,606,854 | A | 8/1986 | Ozawa et al. |
| 4,615,998 | A | 10/1986 | Le Quan et al. |
| 5,292,837 | A | 3/1994 | Heinrich et al. |
| 5,376,706 | A | 12/1994 | Barsotti et al. |
| 5,494,171 | A | 2/1996 | Kazamoto et al. |
| 5,728,912 | A | 3/1998 | Saqualain Haider Rizvi et al. |
| 5,792,895 | A | 8/1998 | Commereuc et al. |
| 5,811,618 | A | 9/1998 | Wu |
| 5,856,612 | A | 1/1999 | Araki et al. |
| 5,877,376 | A | 3/1999 | Commereuc et al. |
| 6,184,428 | B1 | 2/2001 | Zahoor et al. |
| 6,710,005 | B1 * | 3/2004 | Guo ...................... B01J 31/143 |
| | | | 502/103 |
| 6,767,975 | B1 | 7/2004 | Liu |
| 6,903,042 | B2 | 6/2005 | Drochon et al. |
| 7,122,497 | B1 * | 10/2006 | Nagy ...................... C08F 10/00 |
| | | | 502/103 |
| 7,157,532 | B2 | 1/2007 | Payer et al. |
| 7,297,832 | B2 | 11/2007 | Blann et al. |
| 7,300,904 | B2 | 11/2007 | Dixon et al. |
| 7,329,635 | B2 | 2/2008 | Dickakian et al. |
| 7,361,623 | B2 | 4/2008 | Dixon et al. |
| 7,638,597 | B2 | 12/2009 | Etherton et al. |
| 7,919,569 | B2 | 4/2011 | Xu et al. |
| 7,964,763 | B2 | 6/2011 | Dixon et al. |
| 8,227,653 | B2 | 7/2012 | Weber et al. |
| 8,252,871 | B2 | 8/2012 | Aliyev et al. |
| 10,280,125 | B2 | 5/2019 | Sogo et al. |
| 10,471,416 | B2 | 11/2019 | Im et al. |

(Continued)

FOREIGN PATENT DOCUMENTS

| CN | 101189270 A | 5/2008 |
| CN | 102807632 A | 12/2012 |

(Continued)

OTHER PUBLICATIONS

AlJaralla et al. "Dimerization of Ethylene to Butene-1" Catalysis Today, 14 (1992) 1-124, 121 pgs.
Bariashier et al. "Recent advances in homogeneous chromium catalyst design for ethylene tri-, tetra-, oligo- and polymerization" Coordination Chemistry Reviews 385 (2019) 208-229, 22 pgs.
Bartlett et al. "Triptycene (9,10-o-Benzenoanthracene)" Contribution from the Converse Memorial Laboratory of Harvard University, Nov. 1942, 5 pgs.
Blann et al. "Ethylene tetramerisation: Subtle effects exhibited by N-substituted diphosphinoamine ligands" Journal of Catalysis 249 (2007) 244-249, 6 pgs.
Bollmann et al. "Ethylene Tetramerization: A New Route to Produce 1-Octene in Exceptionally High Selectivities" J. Am. Chem. Soc. 2004, 126, 2 pgs.
Elowe et al. "Nitrogen-Linked Diphosphine Ligands with Ethers Attached to Nitrogen for Chromium Catalyzed Ethylene Tri- and Tetramerizations" Arnold and Mabel Beckman Laboratories of Chemical Synthesis, 8 pgs.

(Continued)

*Primary Examiner* — Ali Z Fadhel
(74) *Attorney, Agent, or Firm* — Dinsmore & Shohl LLP

(57) ABSTRACT

Catalyst systems suitable for tetramerizing ethylene to form 1-octene may include a catalyst having a structure according to Formula (VI) or Formula (VII). In Formulas (VI) and (VII), X is a halogen, a ($C_2$-$C_{30}$) carboxylate, acetylacetonate, or a ($C_1$-$C_{30}$) hydrocarbyl; $L_1$ is a neutral coordinating ligand; n is an integer from 0 to 6; Y is a ($C_6$-$C_{20}$)fluorine-substituted aryl, a ($C_6$-$C_{20}$)fluorine-substituted aryloxy, or a ($C_1$-$C_{20}$)fluorine-substituted alkoxy; and L∩L is a bidentate chelating ligand. The catalyst system may also include an aluminum containing agent which includes a reaction product of an organoaluminum compound and an antifouling compound. The antifouling compound may include one or more polyether alcohols or one or more non-polymeric ethers.

16 Claims, No Drawings

(56) References Cited

U.S. PATENT DOCUMENTS

| | | | |
|---|---|---|---|
| 11,104,621 B2 | 8/2021 | Khawaji et al. | |
| 2003/0109766 A1 | 6/2003 | Commereuc et al. | |
| 2004/0259720 A1 | 12/2004 | Sato et al. | |
| 2005/0288470 A1 | 12/2005 | Benham et al. | |
| 2007/0027276 A1 | 2/2007 | Cann et al. | |
| 2009/0105488 A1 | 4/2009 | Cheng et al. | |
| 2010/0113257 A1 | 5/2010 | Kreishcher et al. | |
| 2010/0190939 A1 | 7/2010 | Fritz et al. | |
| 2010/0274065 A1 | 10/2010 | Sydora | |
| 2012/0029258 A1 | 2/2012 | Al-Masned et al. | |
| 2012/0172645 A1 | 7/2012 | Sydora | |
| 2013/0123443 A1 | 5/2013 | Siraux et al. | |
| 2013/0303817 A1 | 11/2013 | Shaik et al. | |
| 2014/0088331 A1 | 3/2014 | Rolland | |
| 2014/0250835 A1 | 9/2014 | Prabhu et al. | |
| 2015/0087873 A1 | 3/2015 | Overett et al. | |
| 2015/0141605 A1 | 5/2015 | Bradin | |
| 2016/0122371 A1 | 5/2016 | Lee et al. | |
| 2016/0311950 A1 | 10/2016 | Batinas-Geurts et al. | |
| 2016/0367977 A1* | 12/2016 | Shaikh | B01J 31/04 |
| 2017/0007994 A1* | 1/2017 | Lucciulli | B01J 37/04 |
| 2017/0197892 A1* | 7/2017 | Khawaji | C07C 2/32 |
| 2017/0274356 A1 | 9/2017 | Cann et al. | |
| 2018/0327332 A1* | 11/2018 | Sogo | C07C 2/32 |
| 2019/0308179 A1 | 10/2019 | Lee et al. | |

FOREIGN PATENT DOCUMENTS

| | | |
|---|---|---|
| CN | 103665201 A | 3/2014 |
| CN | 103724149 A | 4/2014 |
| CN | 107778388 A | 3/2018 |
| EP | 0135441 A1 | 3/1985 |
| EP | 0181954 A1 | 5/1986 |
| EP | 0221206 A1 | 5/1987 |
| EP | 0352856 A1 | 1/1990 |
| EP | 2738151 A1 | 6/2014 |
| EP | 3536696 A1 | 9/2019 |
| EP | 3640232 A1 | 4/2020 |
| EP | 3805240 A1 | 4/2021 |
| JP | H0288529 A | 3/1990 |
| RU | 2561921 C1 | 9/2015 |
| WO | 2010092554 A1 | 8/2010 |
| WO | 2012013805 A1 | 2/2012 |
| WO | 2013154446 A1 | 10/2013 |
| WO | 2013168106 A1 | 11/2013 |
| WO | 2015087303 A2 | 6/2015 |
| WO | 2015087304 A2 | 6/2015 |
| WO | 2015087305 A2 | 6/2015 |
| WO | 2015118462 A1 | 8/2015 |
| WO | 2017120310 A1 | 7/2017 |
| WO | 2018106764 A1 | 6/2018 |
| WO | 2019235799 A1 | 12/2019 |

OTHER PUBLICATIONS

Farrell "Developments in Linear Alpha Olefin (LAO) Comonomer Technologies for Polyethylene" Chemsystems PERP 2011S11,May 2012, 7 pgs.

Fei et al. "Influence of the functional group on the synthesis of aminophosphines, diphosphinoamines and iminobiphosphines" Dalton Trans., 2003, 2772-2779, 8 pgs.

Forestiere et al. "Oligomerization of Monoolefines by Homgeneous Catalysts" Oil & Gas Science and Technology—Rev. IFP, vol. 64 (2009) No. 6, 19 pgs.

Hennico "Butene-1 is made from ethylene" Hydrocarbon Processing, Journal vol. 69:3, 1990, Abstract Only, 2 pgs.

Karin et al. "Removal of Trace Elemental Impurities from Polyethylene by Nitric Acid" Analytical Chemistry, vol. 47, No. 13, Nov. 1975, 4 pgs.

Killian et al. "The use of bis(diphenylphosphino)amines with N-aryl functionalities in selective ethylene tri- and tetramerisation" Journal of Molecular Catalysis A: Chemical 270 (2007) 214-218, 5 pgs.

Kim et al. "Ligand Modification for Selectivity Control in Selective Ethylene Oligomerization" Macromol. Res., 26(4), 341-345(2018), 5 pgs.

Kim et al. "MAO-free and extremely active catalytic system for ethylene tetramerization" Appl Organometal Chem. 2019;33:e4829, 13 pgs.

Mole "Organoaluminium Compounds" Aust. J. Chem., 1966, 19, 381-6, 6 pgs.

Obrey et al. "A Lewis Base Promoted Alkyl/Alkoxide Ligand Redistribution: Reaction of [Me2Al(u-OCPh3)]2 with THF" Organometallics 2001, 20, 5119-5124, 6 pgs.

Pietrzykowski et al. "Reactions of methyl- and ethylaluminium compounds with alkoxyalcohols. The influence of alkoxyalchohol substituents on the structure of the complexes formed" Inorganica Chimica Acta 334 (2002) 385-394, 10 pgs.

Smith et al. "Ethylene Dimerization over Supported Titanium Alkoxides" Journal of Catalysis 105, 187-198 (1987), 12 pgs.

Sydora "Selective Ethylene Oligomerization" Organometallics 2019, 38, 997-1010, 14 pgs.

Weidman et al. "Triptycene-based copolyimides with tailored backbone rigidity for enhanced gas transport" Polymer 126(2017) 314-232, 10 pgs.

Chinese First Office Action dated Nov. 6, 2019, pertaining to Chinese Patent Application No. 201680035981.0.

European Extended Search Report dated Dec. 20, 2019, pertaining to European Patent Application No. 19188473.3.

India Examination Report dated Apr. 27, 2020, pertaining to Indian Patent Application No. 201837025980.

Translation of Japanese Office Action dated Jul. 8, 2020, pertaining to Japanese Patent Application No. 2017-565808.

Translation of Japanese Office Action dated Jan. 6, 2021, pertaining to Japanese Patent Application No. 2018-535418.

Translation of Russian Office Action dated Feburary 27, 2020, pertaining to Russian Patent Application No. 2018128919.

Final Office Action dated Feb. 25, 2021, pertaining to U.S. Appl. No. 15/181,923.

Final Office Action dated May 10, 2019, pertaining to U.S. Appl. No. 15/181,923.

Non-Final Office Action dated Aug. 20, 2020, pertaining to U.S. Appl. No. 15/181,923.

Non-Final Office Action dated Sep. 4, 2019, pertaining to U.S. Appl. No. 15/181,923.

Non-Final Office Action dated Dec. 13, 2018, pertaining to U.S. Appl. No. 15/181,923.

Invitation to Pay Additional Fees dated Sep. 15, 2016, pertaining to Int'l Patent Application No. PCT/US2016/037366.

International Search Report and Written Opinion dated Nov. 21, 2016, pertaining to Int'l Patent Application No. PCT/US2016/037366.

Final Office Action dated Feb. 28, 2020, pertaining to U.S. Appl. No. 15/393,865.

Final Office Action dated Aug. 10, 2018, pertaining to U.S. Appl. No. 15/393,865.

Notice of Allowance and Fees Due dated Apr. 28, 2021, pertaining to U.S. Appl. No. 15/393,865.

Non-Final Office Action dated Jan. 4, 2021, pertaining to U.S. Appl. No. 15/393,865.

Non-Final Office Action dated Jan. 11, 2019, pertaining to U.S. Appl. No. 15/393,865.

Non-Final Office Action dated Mar. 13, 2018, pertaining to U.S. Appl. No. 15/393,865.

International Search Report and Written Opinion dated Jun. 8, 2017, pertaining to Int'l Patent Application No. PCT/US2017/012299.

Non-Final Office Action dated Oct. 19, 2018, pertaining to U.S. Appl. No. 15/830,800.

International Search Report and Written Opinion dated Feb. 20, 2018, pertaining to Int'l Patent Application No. PCT/US2017/064841.

Notice of Allowance and Fees due dated Sep. 10, 2020, pertaining to U.S. Appl. No. 16/134,207.

Non-Final Office Action dated Mar. 30, 2020, pertaining to U.S. Appl. No. 16/134,207.

International Search Report and Written Opinion dated Jan. 3, 2019, pertaining to Int'l Patent Application No. PCT/US2018/051514.

(56) References Cited

OTHER PUBLICATIONS

International Search Report and Written Opinion dated Mar. 18, 2021, pertaining to Int'l Patent Application No. PCT/US2020/059974.

Singapore Office Action dated Aug. 10, 2020, pertaining to Singapore Patent Application No. 11201805653U.

Notification of Transmittal of the International Search Report and the Written Opinion of the International Searching Authority, or the Declaration dated Mar. 15, 2022 pertaining to International application No. PCT/US2021/061123 filed Nov. 30, 2021, 20 pages.

Notification of Transmittal of the International Search Report and the Written Opinion of the International Searching Authority, or the Declaration dated Mar. 11, 2022 pertaining to International application No. PCT/US2021/061117 filed Nov. 30, 2021, 23 pages.

Kim, Eun Ho et al. "Methylaluminoxane-Free Chromium Catalytic System for Ethylene Tetramerization", ACS Omega, vol. 2, No. 3, Mar. 31, 2017, pp. 765-773.

Wang, Tao et al. "Mixed aluminoxanes: efficient cocatalysts for bisphosphineamine/Cr(III) catalyzed ethylene tetramerization toward 1-octene", Applied Petrochemical Research, vol. 5, No. 2, Mar. 1, 2015, pp. 143-149.

International Search Report and Written Opinion dated Feb. 28, 2022 pertaining to International application No. PCT/US2021/060330 filed Nov. 22, 2021, 17 pages.

International Search Report and Written Opinion dated Mar. 1, 2022 pertaining to International application No. PCT/US2021/061115 filed Nov. 30, 2021, 20 pages.

International Search Report and Written Opinion dated Mar. 4, 2022 pertaining to International application No. PCT/US2021/061114 filed Nov. 30, 2021, 20 pages.

International Search Report and Written Opinion dated Mar. 4, 2022 pertaining to International application No. PCT/US2021/061116 filed Nov. 30, 2021, 20 pages.

Tao, Jiang et al., "A series of novel bisphosphinoamine ligands: Synthesis, characterization and application in ethylene tetramerization", Chinese Science Bulletin, Science China Press (SCP) and Springer, CN, vol. 55, No. 33, Nov. 1, 2010, pp. 3750-3754.

Database CA [Online] Chemical Abstracts Service, Columbus, Ohio, US; 2014, Sun, Yueming et al. "Boron- and silicon-bridged bis(diphenylphosphino)-type ligands for chromium-catalyzed ethylene oligomerization", XP002805681, retrieved from STN Database accession No. 2014:525027 abstract & Sun, Yueming et al: "Boron- and silicon-bridged bis(diphenylphosphino)-type ligands for chromium-catalyzed ethylene oligomerization" Chinese Science Bulletin, 59(21), 2613-2617; ISSN: 1001-6538, 2014.

Baojun, Zhang et al., "Cr(III)-Based Catalyst System for Oligomerization of Ethylene to 1-Octene with High Selectivity", Chinese Journal of Catalysis, vol. 28, No. 4, Jan. 1, 2007, pp. 317-320.

Shen, Hongxia Ei Al., "Effects of halide in homogeneous Cr(III)/PNP/MAO catalytic systems for ethylene tetramerization toward 1-octene", Journal of Molecular Catalysis A: Chemical, Elsevier, Amsterdam, NL, vol. 270, No. 1-2, May 7, 2007, pp. 273-277.

\* cited by examiner

CATALYST SYSTEMS

CROSS REFERENCE TO RELATED APPLICATIONS

This application claims the benefit of and priority to U.S. Application Ser. No. 63/119,221 filed on Nov. 30, 2020 and entitled "Catalyst Systems," the entire contents of which are incorporated by reference in the present disclosure. Additionally, this application claims the benefit of and priority to U.S. Application Ser. No. 63/119,136 filed on Nov. 30, 2020 and entitled "Catalyst Systems," the entire contents of which are incorporated by reference in the present disclosure.

TECHNICAL FIELD

Embodiments of the present disclosure generally relate chemical processing and, more particularly, to catalyst systems utilized in such chemical processing.

BACKGROUND

Linear alpha-olefins ("LAOs") were historically produced from cracking of refinery products or products of non-selective oligomerization of ethylene as a broad olefin fraction. Demand for these compounds is rising in North America, Western Europe, and Asia. Currently, there are several industrial processes that produce linear alpha-olefins. Notably, the Shell Higher Olefin Process (SHOP), which has been in operation since 1977, can be used to produce LAOS. The SHOP process employs a combination of oligomerization and olefin metathesis chemistries to produce a variety of LAOs using a Ni-based catalyst. INEOS, a global manufacturer of petrochemicals has also developed a proprietary process for synthesizing a wide range of LAOs with the flexibility to change distributions of products to meet demand.

The demand for short chain alpha olefins, such as 1-octene and 1-hexene, has been rising as well. Specific chain length ranges of alpha-olefins are crucial for specific applications. For example, short chain-lengths (e.g., 1-butene to 1-octene) are used to improve the rheological melt and solid resin properties of polyethylene. The main consumer of 1-octene is the high-volume production of linear low-density polyethylene (LLDPE) and high-density polyethylene (HDPE), which expands each year. Co-monomer alpha-olefin content is 1-2% for HDPE grades and reach up to 30% for some LLDPE grades.

As such, 1-octene is a very important chemical feedstock which is in market demand. Aside from the processes discussed above, various catalysts have been developed for the tetramerization of ethylene to form 1-octene. However, these catalysts have deficiencies in several respects. As such, improved catalysts which are suitable for tetramerization of ethylene to from 1-octene are desired in the industry.

SUMMARY

Fouling, as described herein, refers to the undesirable formation of polymers. Such polymers may form as side-products in the reaction of ethylene to form 1-octene when a catalyst system including chromium is used. However, as described herein, it has been discovered that the utilization of a co-catalyst that is a reaction product of an antifouling compound and an organoaluminum compound, may reduce fouling. As described herein, such antifouling compounds may include one or more polyether alcohols or one or more non-polymeric ethers, and it is believed that the incorporation of this antifouling compound into the catalyst system may be responsible for reduced fouling. Moreover, in some embodiments, the utilization of the co-catalyst described herein may contribute to maintaining the selectivity of 1-octene, or even enhancing the selectivity of 1-octene, as compared with similar catalyst systems that do not include the antifouling compound.

According to one or more embodiments, a catalyst system suitable for tetramerizing ethylene to form 1-octene may include a catalyst having a structure according to Formula (VI) or Formula (VII).

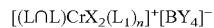  Formula (VI)

  Formula (VII)

In Formulas (VI) and (VII), X is a halogen, a $(C_2-C_{30})$ carboxylate, acetylacetonate, or a $(C_1-C_{30})$ hydrocarbyl; $L_1$ is a neutral coordinating ligand; n is an integer from 0 to 6; Y is a $(C_6-C_{20})$fluorine-substituted aryl, a $(C_6-C_{20})$fluorine-substituted aryloxy, or a $(C_1-C_{20})$fluorine-substituted alkoxy; and L∩L is a bidentate chelating ligand having the structure according to Formula (VIII).

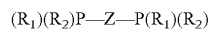  Formula (VIII)

In Formula (VIII), each $R_1$ and $R_2$ is independently chosen from a $(C_1-C_{50})$ alkyl group or a $(C_6-C_{50})$ aryl group, and Z is a $(C_2-C_{50})$ alkylene group, a $(C_6-C_{50})$ arylene group, —N$(R_8)$—, —P$(R_8)$—, —B$(R_8)$—, or —Si$(R_8)_2$— that links the two P atoms, where $R_8$ is a $(C_1-C_{50})$ alkyl group or a $(C_6-C_{50})$ aryl group. The catalyst system may further comprise at least one aluminum containing agent comprising a reaction product of an organoaluminum compound and an antifouling compound. The antifouling compound may comprise one or more polyether alcohols or one or more non-polymeric ethers.

According to one or more embodiments, a method of making a catalyst system suitable for tetramerizing ethylene to form 1-octene may include mixing a chromium compound, an anion-containing compound, a bidentate chelating ligand, and an aluminum containing agent to form the catalyst system. The aluminum containing agent is a reaction product of an organoaluminum compound and an antifouling compound, and wherein the antifouling compound comprises one or more polyether alcohols or one or more non-polymeric ethers.

Additional features and advantages of the described embodiments will be set forth in the detailed description which follows, and in part will be readily apparent to those skilled in the art from that description or recognized by practicing the described embodiments, including the detailed description which follows, as well as the claims.

DETAILED DESCRIPTION

Described herein are catalysts systems which may be utilized to produce 1-octene from ethylene by tetramerization. Also described herein are methods for utilizing such catalyst systems. The presently described catalyst systems may include a catalyst and a co-catalyst, as are described in detail herein. In one or more embodiments described herein, the catalyst may comprise chromium and, in some embodiments, may be the reaction product of a chromium complex and a ligand. The co-catalyst may be the reaction product of at least an antifouling compound and an organoaluminum compound.

In one or more embodiments, the catalyst systems described herein may be used to selectively oligomerize ethylene to produce 1-octene, while reducing undesirable polymerization, sometimes referred to in this disclosure as "fouling." For example, reactor fouling may occur at least partially due to the formation of solid polyethylene-based residues, which may reduce fluid flow and/or fully block or at least partially block fluids in a reactor system from flowing at a desired rate. Without being bound by any particular theory, it is believed that the incorporation of the antifouling compound into the catalyst system reduces fouling.

It should be understood that the catalyst systems presently described may not completely eliminate fouling during a reaction. However, in one or more embodiments, these catalyst systems reduce fouling as compared with catalyst systems which do not include the antifouling compound as described in the present disclosure. Also, it should be understood that, while the catalyst systems of the present disclosure may be useful in ethylene oligomerization reactions, such as ethylene dimerization to form 1-butene, they may also be useful for the catalysis of other chemical reactions, and the catalyst systems described in this disclosure should not be considered limited in their use to the tetramerization of ethylene to 1-octene. It should further be understood that the antifouling agents described in this disclosure may be incorporated with other catalyst systems which contain, for example, non-chromium based catalysts.

As used in this disclosure, a "catalyst" refers to any substance that increases the rate of a specific chemical reaction. Catalysts described in this disclosure may be utilized to promote various reactions, such as, but not limited to, tetramerization of ethylene to from 1-octene. Catalysts are generally not consumed in a reaction, but as would be understood in the art, may have reduced catalytic activity over time and need to be replaced and/or regenerated.

As used in this disclosure, a "co-catalyst" generally refers to any substance or chemical agent that brings about catalyst in conjunction with one or more catalysts. In some embodiments, a catalyst may have independent catalytic functionality, while in other embodiments, the catalyst may only have substantial catalytic functionality when paired with a co-catalyst. It should be understood that the catalyst and co-catalyst may be, in some embodiments, bonded or formed in a complex, but in other embodiments are not bonded or present in a complex. Some co-catalysts may be said to "activate" a catalyst, which may increase catalytic functionality.

Additionally, as used in this disclosure, a "catalyst system" refers to any catalytically functional collection of chemical species. In some embodiments, a catalyst system may include a catalyst and a co-catalyst. In additional embodiments, a catalyst system may include additional components, such as, for example, additional co-catalysts or non-catalytic additives which may serve other purposes.

As described herein, a "reaction product" refers to a chemical species formed from the reaction of any two or more reactant species. A reaction product may result in a covalent or ionic bond, coordination, or other interaction between reactant species. In some embodiments, two or more reaction products may result from the reaction of the reactant species, and all of these possible produced chemical species are included in the reactant product as described herein.

When used to describe certain carbon atom-containing chemical groups, a parenthetical expression having the form "$(C_x-C_y)$" means that the unsubstituted form of the chemical group has from x carbon atoms to y carbon atoms, inclusive of x and y. For example, a $(C_1-C_{50})$ alkyl group is an alkyl group having from 1 to 50 carbon atoms in its unsubstituted form. In some embodiments and general structures, certain chemical groups may be substituted by one or more substituents. A substituted chemical group defined using the "$(C_x-C_y)$" parenthetical may contain more than y carbon atoms depending on the identity of any substituents. For example, a "$(C_1-C_{50})$ alkyl substituted with exactly one phenyl ($-C_6H_5$)" may contain from 7 to 56 carbon atoms. Thus, in general when a chemical group defined using the "$(C_x-C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom (—H) bonded to a carbon atom or heteroatom of a corresponding unsubstituted compound or functional group is replaced by a substituent. Substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "—H" means a hydrogen or hydrogen radical that is covalently bonded to another atom. "Hydrogen" and "—H" are interchangeable, and unless clearly specified have identical meanings.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus.

The term "cyclohydrocarbyl" means an aromatic or non-aromatic, cyclic hydrocarbyl having at least three carbon atoms, including monocyclic and polycyclic hydrocarbyls, fused and non-fused polycyclic hydrocarbyls, and bicyclic hydrocarbyls, non-aromatic saturated or unsaturated cyclic hydrocarbyls, and substituted or unsubstituted hydrocarbyls.

The term "aryl" means an aromatic hydrocarbon radical, in which the carbon atoms of the aromatic system may be substituted or unsubstituted. Aryls include monocyclic, bicyclic and tricyclic aromatic hydrocarbon radicals. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Non-limiting examples of aryls include phenyl; fluorenyl; tetrahydrofluorenyl; indacenyl; hexahydroindacenyl; indenyl; dihydroindenyl; naphthyl; tetrahydronaphthyl; and phenanthrenyl.

The term "alkyl" means a saturated hydrocarbon radical that may be linear or branched. Accordingly, the term "$(C_1-C_{20})$ alkyl" means a saturated linear or branched hydrocarbon radical of from 1 to 20 carbon atoms that is unsubstituted or substituted. Examples of unsubstituted ($C_1$-$C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

In one or more embodiments, the catalyst comprises chromium. It should be understood that, as contemplated herein, the catalyst may be any chemical compound that includes chromium that is catalytically functional for, without limitation, promoting the selective tetramorization of ethylene to from 1-octene.

In one or more embodiments, the catalyst includes a reaction product of a chromium complex and a boron-containing compound. In some embodiments, the catalyst includes a reaction product of the chromium complex and the boron-containing compound in, for example, an acetonitrile solvent.

In one or more embodiments, the catalyst system includes a reaction product of a chromium complex, a bidentate chelating ligand, an anion-containing compound, and an aluminum containing agent comprising the reaction product of an organoaluminum compound and an antifouling compound. In some embodiments, the catalyst system includes a reaction product of the chromium complex, the bidentate chelating ligand, the anion-continuing compound, and the aluminum containing agent in a solvent, such as, for example, chlorobenzene.

It should be understood that the chromium complexes described herein are not necessarily limited in structure, but at least include chromium. In some embodiments, the chromium complex has a structure according to formula (I):

$$CrX_3(L_1)_n \qquad \text{Formula (I)}$$

In formula (I), each X is independently chosen from a halogen, a ($C_2$-$C_{30}$) carboxylate, acetylacetonate (ACAC), or a ($C_1$-$C_{30}$) hydrocarbyl having or not having at least one of an ether group and an amine group. The term "carboxylate" refers to conjugate base of a carboxylic acid. In some embodiments, each X is fluorine (F), chlorine (Cl), bromine (Br), iodine (I), or combinations of these. In other embodiments, each X is a ($C_1$-$C_{30}$) alkyl group, a ($C_1$-$C_{30}$) alkyl group substituted by at least one of an ether group and an amine group, a ($C_6$-$C_{30}$)aryl group, or a ($C_5$-$C_{30}$)benzyl derivative. For example, X may be ethyl or ortho-(N,N-dimethylamino)benzyl.

In formula (I), each $L_1$ is a neutral coordinating ligand. In one or more embodiments, each L is independently chosen from a ($C_2$-$C_{30}$)nitrile, a ($C_2$-$C_{30}$)cyclic ether, a ($C_2$-$C_{30}$) acyclic ether, or an $H_2O$ ligand. In some embodiments, $L_1$ may be acetonitrile, tetrahydrofuran (THF), diethylether, $H_2O$, or combinations of these. In embodiments, n is an integer of from 0 to 6. In one or more embodiments, n is an integer from 0 to 5, from 0 to 4, from 0 to 3, from 0 to 2, from 0 to 1, from 1 to 6, from 1 to 5, from 1 to 4, from 1 to 3, from 1 to 2, or any combination or subset of these ranges. However, it should be understood that n may vary depending on the method or the neutral coordinating agent added by which the catalyst is prepared. For example, n may vary depending on the degrees of vacuum drying that occurs during preparation.

In some embodiments, the chromium complex may be a chromium (III) chloride tetrahydrofuran complex (i.e., $Cr(THF)Cl_3$).

In one or more embodiments, the catalyst may comprise the reaction product of the chromium compound and an anion-containing compound. It should be understood that the anion-containing compounds, described herein, which may coordinate with chromium of the chromium complex, are not necessarily limited in structure. However, in some embodiments, the anion-containing compound may have a structure according to formula (II) or formula (III):

$$M^+[BY_4]^- \qquad \text{Formula (II)}$$

$$M^+[SO_2Y]^- \qquad \text{Formula (III)}$$

In formula (II) and formula (III), each Y is independently chosen from a ($C_6$-$C_{20}$) fluorine-substituted aryl, a ($C_6$-$C_{20}$) fluorine-substituted aryloxy, or a ($C_1$-$C_{20}$) fluorine-substituted alkoxy. In one or more embodiments, Y is $C_6F_5$, 3,5-$(CF_3)_2C_6H_3$, $OC(CF_3)_3$, or combinations of these. For example, $[BY_4]^-$ may be $[B(C_6F_5)_4]^-$ or $[B((3,5-(CF_3)_2C_6H_3)_4]^-$. Formula (II) and Formula (III) utilizes $M^+$ as a cation. In one or more embodiments, $M^+$ may be a metal inorganic cation. It is contemplated that any suitable metal may be uses as $M^+$. For example, $M^+$ may be $Ag^+$ in one or more embodiments. In one or more embodiments, $M^+$ may be an organic cation. For example, $M^+$ may be $[Ph_3C]$ or $[PhNHR_7R_8]$, where $R_7$ and $R_8$ are any ($C_1$-$C_{20}$) hydrocarbyl.

In one or more embodiments, the reaction product of the chromium complex and the anion-containing compound is a chromium trivalent compound. In some embodiments, the chromium trivalent compound includes a non-coordinating anion and a chromium trivalent cation. In some embodiments, the chromium trivalent compound has a structure according to formula (IV) or formula (V):

$$[X_2Cr(L_1)_n]^+[BY_4]^- \qquad \text{Formula (IV)}$$

$$[X_2Cr(L_1)_n]^+[SO_2Y]^- \qquad \text{Formula (V)}$$

In formula (IV) and formula (V), X, $L_1$, n, and Y are the same as described previously with regard to formulas (I), (II), and (III).

In one or more embodiments, the catalyst may include the reaction product of a chromium trivalent compound having a structure according to formula (IV) or (V) and a bidentate chelating ligand. In some embodiments, the catalyst may include the reaction product of the chromium trivalent compound having a structure according to formula (IV) or (V) and the bidentate chelating ligand in, for example, a dichloromethane solvent. In such embodiments, one or more of the neutral coordinating ligands ($L_1$) of the chromium trivalent compound having a structure according to formula (IV) or (V) are substituted with the bidentate chelating ligand such that the resulting chromium trivalent compound has a structure according to formula (VI) or formula (VII):

$$[(L\cap L)CrX_2(L_1)_n]^+[BY_4]^- \qquad \text{Formula (VI)}$$

$$[(L\cap L)CrX_2(L_1)_n]^+[SO_2Y]^- \qquad \text{Formula (VII)}$$

In formula (IV), X, $L_1$, n, and Y are the same as described previously with regard to formulas (I) to (V). In formulas (VI) and (VII) L∩L is a bidentate chelating ligand. In one or more embodiments, the bidentate chelating ligand is an organic compound having at least two atoms capable of coordinating with a metal. Examples of atoms capable of coordinating with a metal include phosphorus (P), nitrogen (N), oxygen (O), and combinations of these. In some embodiments, the bidentate chelating ligand has a structure according to formula (VIII):

$(R_1)(R_2)P-Z-P(R_1)(R_2)$　　　Formula (VIII)

In formula (V), each $R_1$ and $R_2$ is independently chosen from a $(C_1-C_{50})$ alkyl group or a $(C_6-C_{50})$ aryl group; and Z is a $(C_2-C_{50})$ alkylene group, a $(C_6-C_{50})$ arylene group, or $-N(R_7)-$, $-P(R_7)-$, $-B(R_7)-$, or $-Si(R_7)_2-$ that links the two P atoms, where $R_7$ is a $(C_1-C_{50})$ alkyl group or a $(C_6-050)$ aryl group. The term "alkylene" refers to an alkyl comprise at least one unsaturated bond. The term "arylene" refers to a bivalent aryl. Without being bound by any particular theory, it is believed that chromium trivalent compounds that include a bidentate chelating ligand having a structure according to formula (V) provide increased catalytic activity and selectivity for 1-octene when used in ethylene tetramerization processes.

Without intending to be bound by theory, the bidentate chelating ligand may determine the electron density and stereo factors of the catalyst center. This may allow the catalyst to selectively oligomerize ethylene to the desired products, such as 1-octene. The bidentate chelating ligand may affect the stability of the catalyst, including the catalytic center and its surrounding environment. Furthermore, the bidentate chelating ligand may affect the activity and selectivity of the catalyst.

In one or more embodiments, the bidentate chelating ligand has a structure according to formula (VIII), where $R_1$ and $R_2$ are phenyl, and Z is $-N(R_7)-$ that links the two P atoms, where $R_7$ is a $(C_1-C_{50})$ alkyl group or a $(C_6-C_{50})$ aryl group. In such embodiments, the bidentate chelating ligand may be produced by reacting $Ph_2PCl$ and $R_7NH_2$. In some embodiments, the bidentate chelating ligand is $CH_3(CH_2)_5 C(H)(Me)N(PPh_2)_2$. Without being bound by any particular theory, it is believed that embodiments where $R_7$ has 18 or more carbon atoms may be more suitable for use in large-scale ethylene tetramerization processes because the solubility of the resulting catalyst in aliphatic hydrocarbon solvents is improved.

In some embodiments, each $R_1$ and $R_2$ bonded to a single P may be bonded such that a cyclic moiety including P is formed. In one or more embodiments, $R_1$, $R_2$, and P may form a phospholane group. As described herein, a "phospholane group" refers to a cyclic organophosphorous compound comprising a five membered ring including phosphorous and four carbon atoms. In some embodiments, the phospholane compound may be unsubstituted or may be substituted by one or more hydrocarbyl groups. Cyclic moieties that may be formed from $R_1$ and P in some embodiments are depicted in formulas (IX) to (XVI).

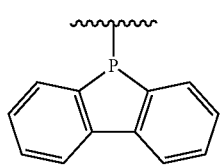

Formula (IX)

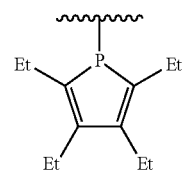

Formula (X)

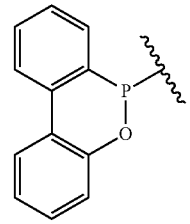

Formula (XI)

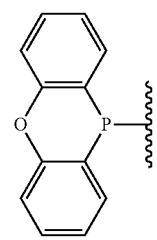

Formula (XII)

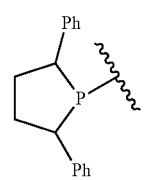

Formula (XIII)

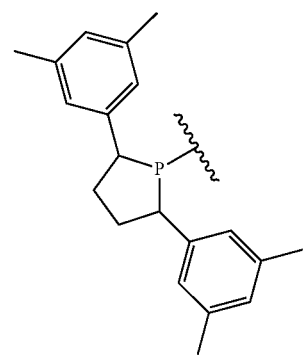

Formula (XIV)

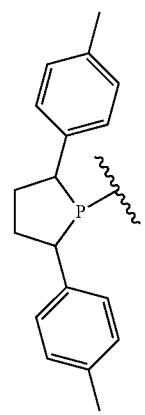

Formula (XV)

Formula (XVI)

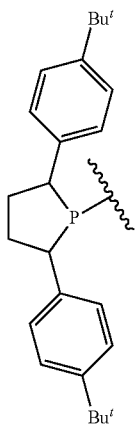

As described herein, the catalyst system also includes an aluminum containing agent. In one or more embodiments, the aluminum containing agent may function as a co-catalyst, as described hereinabove, in the catalyst system. In the embodiments described herein, the aluminum containing agent may be the reaction product of an organoaluminum compound and the antifouling compound. It should be understood that the organoaluminum compound may comprise multiple chemical species, or a single chemical species. Likewise, the antifouling compound may comprise multiple chemical species, or a single chemical species.

In one or more embodiments, the aluminum containing agent may be formed from a organoaluminum compound. As described herein, an "organoaluminum compound" refers to any chemical compound that includes at least one aluminum atom and any organic moiety. It should be appreciated that the organoaluminum compound may include several chemical species, or may be a single chemical species.

In some embodiments, the organoaluminum compound may be an alkyl aluminum compound. The aluminum alkyl compounds described herein may have a generalized structure shown in formula (XVII):

Formula (XVII)

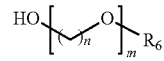

where $R_3$, $R_4$, and $R_5$ may each be a hydrogen atom, a $(C_1-C_{20})$ hydrocarbyl group, or a $(C_1-C_{20})$ heterohydrocarbyl group. In embodiments, the $(C_1-C_{20})$ hydrocarbyl group may be a substituted or unsubstituted $(C_1-C_{20})$ linear or branched hydrocarbyl group. In embodiments, the $(C_1-C_{20})$ heterohydrocarbyl group may be a substituted or unsubstituted $(C_1-C_{20})$ linear or branched heterohydrocarbyl group. In one or more embodiments, $R_3$, $R_4$, and $R_5$ may each be a hydrogen or a linear or branched $(C_1-C_{20})$ alkyl group. In additional embodiments, the alkyl aluminum compound may be an aluminoxane structure (i.e., a partial hydrolysate of trialkylaluminum compounds). For example, and not by way of limitation, suitable aluminum alkyl compounds may include triethylaluminum, tripropylaluminum, tri-iso-butyl-aluminum, diisobutylaluminium hydride, and trihexylaluminum. In one or more embodiments, the organoaluminum compound of the catalyst system may comprise, consist essentially of, or consist of any of these compounds.

In one or more embodiments, the organoaluminum compound may comprise one or more of trimethylaluminium, triethylaluminum, tripropylaluminum, tri-iso-butylaluminum, diisobutylaluminium hydride, trihexylaluminum, tri-n-octylaluminium, methyl aluminium dichloride, ethylaluminium dichloride, dim ethyl aluminium chloride, diethyl aluminium chloride, aluminium isopropoxide, ethylaluminiumsesquichloride, methylaluminiumsesquichloride, methylaluminoxane (MAO), ethylaluminoxane (EAO), and modified methylaluminoxane (MMAO).

Without intending to be bound by theory, the alkyl aluminum compound may be operable to activate the chromium trivalent compound. Furthermore, the alkyl aluminum compound may be operable to alkylate the chromium trivalent compound.

In one or more embodiments, the aluminum containing agent may be formed from an antifouling compound. As described herein, an "antifouling compound" refers to any chemical compound that decreases fouling by polymer production. It should be appreciated that the antifouling compound may include several chemical species, or may be a single chemical species.

In one or more embodiments, the antifouling compound may be a polyether alcohol. In some embodiments, the polyether alcohol may include monomer units comprising one or more carbon chains separating ether moieties. For example, the polyether alcohols described herein may have a generalized structure shown in formula (XVIII):

Formula (XVIII)

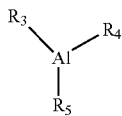

In formula (XV), $R_6$ is chosen from an unsubstituted hydrocarbyl group or a substituted hydrocarbyl group; m is an integer of from 1 to 100; and n is an integer from 1 to 20. In some embodiments, $R_6$ may be an unsubstituted hydrocarbyl group that includes at least 1 carbon atom, at least 2 carbon atoms, at least 3 carbon atoms, at least 4 carbon atoms, at least 5 carbon atoms, at least 6 carbon atoms, at least 7 carbon atoms, at least 8 carbon atoms, at least 8 carbon atoms, at least 9 carbon atoms, at least 10 carbon atoms, at least 11 carbon atoms, or at least 12 carbon atoms. In some embodiments, m is an integer of from 1 to 75, from 1 to 50, from 1 to 25, from 25 to 100, from 25 to 75, from 25 to 50, from 50 to 100, from 50 to 75, or from 75 to 100. In some embodiments, n is an integer of from 1 to 15, from 1 to 10, from 1 to 5, from 5 to 20, from 5 to 15, from 5 to 10, from 10 to 20, from 10 to 15, or from 15 to 20.

Without being bound by any particular theory, it is believed that the reaction between the organoaluminum compound and the antifouling compound may produce various chemical compounds. An example reaction of the aluminum alkyl compound of formula (XVII) and the polyether alcohol of formula (XVIII) is shown in reaction scheme (I):

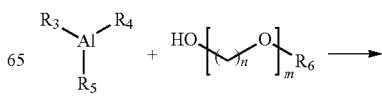

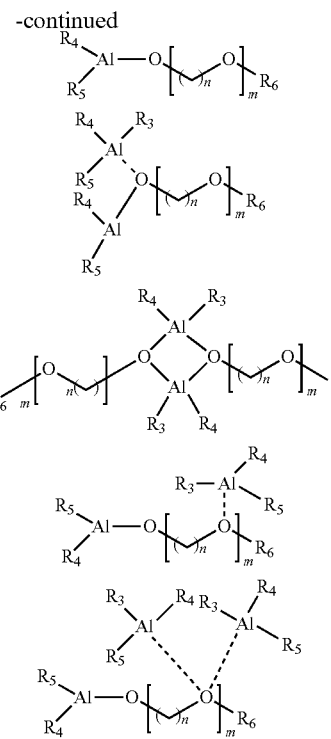

In some embodiments, the antifouling compound may include one or more non-polymeric ethers. The non-polymeric ethers may include cyclic non-polymeric ethers such as, but not limited to, tetrahydrofuran (THE), a dioxane, a tetrahydropyran (THP), or combinations of these. As described herein, a "non-polymeric" ethers refers to any chemical compound that includes one or more ethers but do not include long ether polymer chains. Generally, such non-polymeric ethers comprise one or two ether moieties, and comprise less than 10 ether moieties.

Without intending to be bound by theory, the reaction products of the organoaluminum compound and the antifouling compound may affect the ion-pair of the metal activation center of the catalyst. This may affect the coordination of ethylene with the metal activation center and the degree of chain-transfer predominant with respect to chain propagation. By controlling the chain propagation, the reaction products of the organoaluminum compound and the antifouling compound may increase the product selectivity of 1-octene and reduce the production of large polymers, resulting in reduced fouling. Furthermore, it is contemplated that in one or more embodiments the reactions between the quaternary salt and the organoaluminum compound are relatively fast and that there are little to no free quaternary salts remaining in the catalytic system once the quaternary salt and organoaluminum compound react.

It should be understood that the aluminum containing agents contemplated herein may include a number of different chemical species. However, as described in embodiments herein, these aluminum containing agent species share certain structures and can be commonly classified by moiety or structure.

In one or more embodiments described herein, the antifouling compound and organoaluminum compound may have a molar ratio of from 0.001 to 1, such as from 0.01 to 0.1. For example, according to embodiments, the molar ratio of antifouling compound to organoaluminum compound may be from 0.001 to 0.01, from 0.01 to 0.02, from 0.02 to 0.03, from 0.03 to 0.04, from 0.04 to 0.05, from 0.05 to 0.06, from 0.06 to 0.07, from 0.07 to 0.08, from 0.08 to 0.09, from 0.09 to 0.1, from 0.1, to 0.2, from 0.2 to 0.3, from 0.3 to 0.4, from 0.4 to 0.5, from 0.5 to 0.6, from 0.6 to 0.7, from 0.7 to 0.8, from 0.8 to 0.9, from 0.9 to 1, or any combination of these ranges, such as any subgroup encompassed by any combination of these ranges.

According to one or more embodiments, the catalyst system may further comprise additional co-catalysts and/or additives. It should be understood that these additional co-catalysts and/or additives are optional and are not included in all embodiments described herein. Examples of additional co-catalysts and/or additives include, without limitation, any of the organoaluminium compounds described herein which form the co-catalyst (e.g. diisobutylaluminium hydride or and TEAL) could also be added to the catalyst system. Such additional co-catalysts may be present if an excess amount of organoaluminum compound is added to form the co-catalyst, such that all antifouling complex is reacted by excess organoaluminum compound remains in the solution.

In one or more embodiments, methods for forming the catalyst system include mixing a chromium complex, a bidentate chelating ligand, an anion-containing compound, and an aluminum containing agent comprising the reaction product of an organoaluminum compound and an antifouling compound. In one or more embodiments, the chromium complex, bidentate chelating ligand, anion-containing compound, and aluminum containing agent may be mixed in the presence of a solvent, such as chlorobenzene. The chromium complex, bidentate chelating ligand, anion-containing compound, and aluminum containing agent may form a reaction product when mixed, and such reaction product may be a catalyst system suitable for tetramerizing ethylene to 1-octene.

It should be understood that the chromium complex, bidentate chelating ligand, anion-containing compound, and aluminum containing agent may be mixed simultaneously or in any order. For example, in one or more embodiments, the chromium complex, bidentate chelating ligand, and anion-containing compound may be mixed to form a catalyst, and subsequently the aluminum containing agent may be mixed with the catalyst to form the catalyst system. In one or more embodiments, the chromium complex, the bidentate chelating ligand and the aluminum containing agent may be mixed initially and that mixture may be subsequently mixed with the anion-containing compound to form the catalyst system.

In one or more embodiments, ethylene may be contacted with the catalyst system described herein to from a product comprising 1-octene. Contacting may generally include any mixing, combining, etc. of the reactant ethylene with the catalyst system. In one or more embodiments, the catalyst and aluminum containing agent may be separately prepared, and then combined, prior to contacting of the catalyst system with ethylene. In one or more embodiments, the ethylene may be contacted with the catalyst system in the presence of hydrogen.

The reaction may be performed as a batch reaction or as a continuous process reaction, such as a continuous stir tank reactor process. According to further embodiments, the pressure of the reactor may be from 5 bar to 120 bar (such as from 20 bar to 40 bar), and the reactor temperature may be from 25° C. to 180° C. (such as from 30° C. to 60° C.). However, process conditions outside of these ranges are contemplated, especially in view of the specific design of the reactor system and concentrations of the reactants and catalysts.

It should be understood that, in one or more embodiments, similar or identical catalyst systems which do not include the antifouling compound may exhibit increased fouling. In one or more embodiments, the introduction of the antifouling agent into a catalyst system may suppress polymer formation while not greatly reducing catalytic activity of 1-octene formation. In one embodiment, polymer formation (fouling) may be reduced by at least 5%, 10%, 20%, 30%, 40%, 50%, 60%, 70%, 80%, 90%, or even 95% by the inclusion of an antifouling compound. In one embodiment, 1-octene production may be increased, stay the same, or may decrease by less than or equal to 50%, 40%, 30%, 20%, 10% or even 5% by the inclusion of an antifouling compound. In some embodiments, antifouling compounds may both reduce the polymer formation (such as by at least 5%, 10%, 20%, 30%, 40%, 50%, 60%, 70%, 80%, 90% or even 95%)) and increase, not effect, or decrease 1-octene production rate by less than or equal to 50%, 40%, 30%, 20%, 10% or even 5%. Reduction in polymer formation rates and catalytic activity on a percentage basis are based on catalyst systems which are formed from the antifouling compounds described herein as compared with catalyst systems which are void of an antifouling compound.

EXAMPLES

The various aspects of the present disclosure will be further clarified by the following examples. The examples are illustrative in nature and should not be understood to limit the subject matter of the present disclosure.

Catalyst Production Procedure

In the following examples, the catalyst has a structure according to formula (XIX):

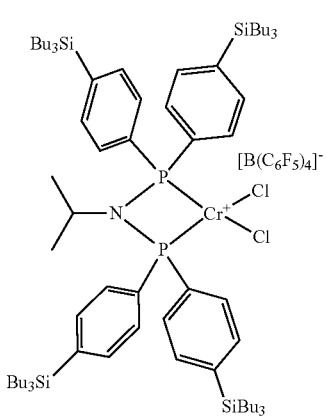

Formula (XIX)

The catalyst was produced by the method described in U.S. patent application Ser. No. 16/346,735, the entire contents of which are incorporated by reference in their entirety.

Co-Catalyst Production Procedure

In the following examples, each co-catalyst was produced using the same general method. The general method included reacting an antifouling compound (AFC) and diisobutylaluminum hydride (DIBAL) (i.e., an organoaluminum compound) in an oxygen and moisture-free atmosphere to produce a co-catalyst. Specifically, the AFC was added to 105 milligrams (mg) of a solution of DIBAL in methylcyclohexane (MCH) (1.0 molarity) such that the molar ratio of the AFC to aluminum (AFC:Al) was from 0.001 to 1 or from 0.01 to 0.1.

Ethylene Tetramerization Procedure

In the following examples, an ethylene tetramerization process (also referred to as a run) was conducted using the same general procedure. Each run was conducted in a 250 milliliter (ml) autoclave reactor unit. Before each run, the autoclave reactor unit was vacuum purged with ultrapure nitrogen to remove oxygen and moisture, which may be detrimental to the ethylene tetramerization reaction, and then filled with a desired amount of anhydrous MCH as a solvent. Once the autoclave reactor unit was prepared, 3.7 milligrams (mg) of the catalyst dissolved in 100 ml of anhydrous MCH and the co-catalyst were separately injected into the autoclave reactor unit. The amount of co-catalyst injected into the autoclave reactor unit was determined based on a desired molar ratio of co-catalyst to catalyst. Subsequently, approximately 3 bar of ultrapure molecular hydrogen was charged to the autoclave reactor unit, which was then heated to a temperature of from 30° C. to 60° C. In order to initiate the run, from 20 bar to 40 bar of ethylene was charged to the autoclave rector unit. Once a desired run time was reached, the run was terminated by injecting 2.0 ml of methanol into the autoclave reactor unit, which was then depressurized. Any solid polymer produced was collected from the autoclave reactor unit, filtered, dried overnight in an oven at 110° C., and weighed.

Examples 1 and 2

In Examples 1 and 2, a co-catalyst was produced that included an AFC having a structure according to formula (XX):

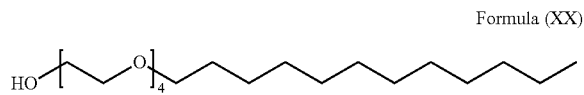

Formula (XX)

Ethylene tetramerization processes were then conducted using the catalyst and co-catalyst in various molar ratios. The results of Examples 1 and 2 are reported in Table 1.

Comparative Example 3

Comparative Example 3 was conducted in a manner similar to Example 1, except that the DIBAL was injected into the autoclave reactor unit without the addition of an AFC (i.e., no co-catalyst was produced). The results of Comparative Example 3 are reported in Table 1.

TABLE 1

| Example | Catalyst (mmol) | DIBAL (mmol) | Molar Ratio (Co-Cat:Cat) | Activity (mol 1-octene/mol catalyst/hour) | 1-Hexene Selectivity (mol. %) | 1-Octene Selectivity (mol. %) | Polymer (wt. %) |
|---|---|---|---|---|---|---|---|
| Example 1 | 0.001 | 0.150 | 0.05 | 2,507,600 | 32.78 | 47.38 | 0.98 |
| Example 2 | 0.001 | 0.150 | 0.2 | 2,125,351 | 34.50 | 47.29 | 1.05 |
| Comparative Example 3 | 0.001 | 0.150 | — | 2,649,953 | 19.31 | 62.36 | 2.08 |

Reaction Conditions—Temperature: 50° C.; $C_2H_4$ Pressure: 20 bar; $H_2$ Pressure: 3 bar; Run Time: 20 min.

As shown in Table 1, the catalyst systems of Examples 1 and 2 each resulted in lower production of polymer than the catalyst system of Comparative Example 3. Accordingly, the catalyst systems of Examples 1 and 2 provide a benefit over the catalyst system of Comparative Example 3 by providing a relatively low polymer selectivity. Furthermore, the catalyst systems of Examples 1 and 2 generally provided comparable activity and selectivity for 1-octene to the catalyst system of Comparative Example 3, despite the activity and selectivity for 1-octene being lower than Comparative Example 3.

In a first aspect of the present disclosure, a catalyst system suitable for tetramerizing ethylene to form 1-octene may include a catalyst having a structure according to Formula (VI) or Formula (VII). In Formulas (VI) and (VII), X is a halogen, a ($C_2$-$C_{30}$) carboxylate, acetylacetonate, or a ($C_1$-$C_{30}$) hydrocarbyl; $L_1$ is a neutral coordinating ligand; n is an integer from 0 to 6; Y is a ($C_6$-$C_{20}$)fluorine-substituted aryl, a ($C_6$-$C_{20}$)fluorine-substituted aryloxy, or a ($C_1$-$C_{20}$)fluorine-substituted alkoxy; and L∩L is a bidentate chelating ligand having the structure according to Formula (VIII). In Formula (VIII), each $R_1$ and $R_2$ is independently chosen from a ($C_1$-$C_{50}$) alkyl group or a ($C_6$-$C_{50}$) aryl group, and Z is a ($C_2$-$C_{50}$) alkylene group, a ($C_6$-$C_{50}$) arylene group, —N($R_7$)—, —P($R_7$)—, —B($R_7$)—, or —Si($R_7$)$_2$— that links the two P atoms, where $R_7$ is a ($C_1$-$C_{50}$) alkyl group or a ($C_6$-$C_{50}$) aryl group. The catalyst system may further comprise at least one aluminum containing agent comprising a reaction product of an organoaluminum compound and an antifouling compound. The antifouling compound may comprise one or more polyether alcohols or one or more non-polymeric ethers.

A second aspect of the present disclosure may include the first aspect, where the catalyst has a structure according to Formula (VI).

A third aspect of the present disclosure may include either the first or second aspect, where the catalyst has a structure according to Formula (VII).

A fourth aspect of the present disclosure may include any of the first to third aspects, where the antifouling compound comprises one or more polyether alcohols.

A fifth aspect of the present disclosure may include any of the first to fourth aspects, where the antifouling compound comprises one or more non-polymeric ethers.

A sixth aspect of the present disclosure includes any of the first through fifth aspects, where each $L_1$ is a ($C_2$-$C_{30}$) nitrile, a ($C_2$-$C_{30}$) cyclic ether, a ($C_2$-$C_{30}$) acyclic ether, or an $H_2O$ ligand.

A seventh aspect of the present disclosure includes any of the first through sixth aspects, where the organoaluminum compound has a structure according to formula (XVII) in which $R_3$, $R_4$, and $R_5$ are each selected from a hydrogen atom, a ($C_1$-$C_{20}$) hydrocarbyl group, and a ($C_1$-$C_{20}$) heterohydrocarbyl group.

An eighth aspect of the present disclosure includes any of the first through seventh aspects, where the organoaluminum compound comprises one or more of trimethylaluminium, triethylaluminum, tripropylaluminum, tri-iso-butylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified methylaluminoxane (MMAO).

A ninth aspect of the present disclosure includes any of the first through eighth aspects, where the molar ratio of the antifouling compound to the organoaluminum compound is from 0.001 to 1.

According to a tenth aspect of the present disclosure, a method for tetramerizing ethylene to form 1-octene may comprise contacting ethylene with a catalyst system of any of the first through ninth aspects to form a product comprising 1-octene.

An eleventh aspect of the present disclosure may include the tenth aspect, where ethylene is formed in conditions of a reactor pressure from 5 bar to 120 bar; and a reactor temperature from 25° C. to 180° C.

According to a twelfth aspect of the present disclosure, a method of making a catalyst system suitable for tetramerizing ethylene to form 1-octene may include mixing a chromium compound, an anion-containing compound, a bidentate chelating ligand, and an aluminum containing agent to form the catalyst system. The aluminum containing agent is a reaction product of an organoaluminum compound and an antifouling compound, and wherein the antifouling compound comprises one or more polyether alcohols or one or more non-polymeric ethers.

A thirteenth aspect of the present disclosure may include the twelfth aspect, where the chromium compound has a structure according to Formula (I). In Formula (I), X is a halogen, a ($C_2$-$C_{30}$) carboxylate, acetylacetonate, or a ($C_1$-$C_{30}$) hydrocarbyl; $L_1$ is a ligand; and n is an integer from 0 to 6.

A fourteenth aspect of the present disclosure may include either the twelfth or thirteenth aspect, where the anion containing compound has a structure according to Formula (II). In Formula (II), Y is a ($C_6$-$C_{20}$)fluorine-substituted aryl, a ($C_6$-$C_{20}$)fluorine-substituted aryloxy, or a ($C_1$-$C_{20}$)fluorine-substituted alkoxy; and $M^+$ is a metal inorganic cation, or an organic cation.

A fifteenth aspect of the present disclosure may include either the twelfth or thirteenth aspect, where the anion containing compound has a structure according to Formula (III). In Formula (III), Y is a ($C_6$-$C_{20}$)fluorine-substituted aryl, a ($C_6$-$C_{20}$)fluorine-substituted aryloxy, or a ($C_1$-$C_{20}$) fluorine-substituted alkoxy; and $M^+$ is a metal inorganic cation, or an organic cation.

A sixteenth aspect of the present disclosure may include any of the twelfth to fifteenth aspects, where the bidentate chelating ligand has the structure according to Formula (VIII). In Formula (VIII), each $R_1$ and $R_2$ is independently chosen from a $(C_1\text{-}C_{50})$ alkyl group or a $(C_6\text{-}C_{50})$ aryl group, and Z is a $(C_2\text{-}C_{50})$ alkylene group, a $(C_6\text{-}C_{50})$ arylene group, —N($R_7$)—, —P($R_7$)—, —B($R_7$)—, or —Si($R_7$)$_2$— that links the two P atoms, where $R_7$ is a $(C_1\text{-}C_{50})$ alkyl group or a $(C_6\text{-}C_{50})$ aryl group.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

Additionally, the term "consisting essentially of" is used in this disclosure to refer to quantitative values that do not materially affect the basic and novel characteristic(s) of the disclosure. For example, a chemical composition "consisting essentially" of a particular chemical constituent or group of chemical constituents should be understood to mean that the composition includes at least about 99.5% of a that particular chemical constituent or group of chemical constituents.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

What is claimed is:

1. A catalyst system suitable for tetramerizing ethylene to form 1-octene, the catalyst system comprising:

a catalyst having the structure:

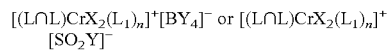

wherein:

X is a halogen, a $(C_2\text{-}C_{30})$ carboxylate, acetylacetonate, or a $(C_1\text{-}C_{30})$ hydrocarbyl;

$L_1$ is a neutral coordinating ligand;

n is an integer from 0 to 6;

Y is a $(C_6\text{-}C_{20})$fluorine-substituted aryl, a $(C_6\text{-}C_{20})$ fluorine-substituted aryloxy, or a $(C_1\text{-}C_{20})$fluorine-substituted alkoxy; and L∩L is a bidentate chelating ligand having the structure:

$(R_1)(R_2)P\text{—}Z\text{—}P(R_1)(R_2)$ wherein:

each $R_1$ and $R_2$ is independently chosen from a $(C_1\text{-}C_{50})$ alkyl group or a $(C_6\text{-}C_{50})$ aryl group; and Z is a $(C_2\text{-}C_{50})$ alkylene group, a $(C_6\text{-}C_{50})$ arylene group, —N($R_7$)—, —P($R_7$)—, —B($R_7$)—, or —Si($R_7$)$_2$— that links the two P atoms, where $R_7$ is a $(C_1\text{-}C_{50})$ alkyl group or a $(C_6\text{-}C_{50})$ aryl group; and At least one aluminum containing agent comprising a reaction product of an organoaluminum compound and an antifouling compound, wherein the antifouling compound comprises one or more polyether alcohols or one or more non-polymeric ethers.

2. The catalyst system of claim 1, wherein the catalyst has the structure:

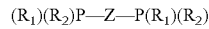

3. The catalyst system of claim 1, wherein the catalyst has the structure:

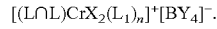

4. The catalyst system of claim 1, wherein the antifouling compound comprises one or more polyether alcohols.

5. The catalyst system of claim 1, wherein the antifouling compound comprises one or more non-polymeric ethers.

6. The catalyst system of claim 1, wherein each $L_1$ is a $(C_2\text{-}C_{30})$ nitrile, a $(C_2\text{-}C_{30})$ cyclic ether, a $(C_2\text{-}C_{30})$ acyclic ether, or an $H_2O$ ligand.

7. The catalyst system of claim 1, wherein the organoaluminum compound has the structure:

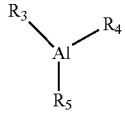

wherein $R_3$, $R_4$, and $R_5$ are each selected from a hydrogen atom, a $(C_1\text{-}C_{20})$ hydrocarbyl group, and a $(C_1\text{-}C_{50})$ heterohydrocarbyl group.

8. The catalyst system of claim 1, wherein the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified methylaluminoxane (MMAO).

9. The catalyst system of claim 1, wherein the molar ratio of the antifouling compound to the organoaluminum compound is from 0.001 to 1.

10. A method for tetramerizing ethylene to form 1-octene, the method comprising contacting ethylene with the catalyst system of claim 1 to form a product comprising 1-octene.

11. The method of claim 10, wherein the ethylene is formed in conditions of:
a reactor pressure from 5 bar to 120 bar; and
a reactor temperature from 25° C. to 180° C.

12. A method of making a catalyst system suitable for tetramerizing ethylene to form 1-octene, the method comprising mixing a chromium compound, an anion-containing compound, a bidentate chelating ligand, and an aluminum containing agent to form the catalyst system, wherein the aluminum containing agent is a reaction product of an organoaluminum compound and an antifouling compound, and wherein the antifouling compound comprises one or more polyether alcohols or one or more non-polymeric ethers.

13. The method of claim 12, wherein the chromium compound has the structure:

$$CrX_3(L_1)_n$$

wherein:
X is a halogen, a $(C_2-C_{30})$ carboxylate, acetylacetonate, or a $(C_1-C_{30})$ hydrocarbyl;
$L_1$ is a ligand; and
n is an integer from 0 to 6.

14. The method of claim 12, wherein the anion containing compound has a structure:

$$M^+[BY_4]^-$$

wherein:
Y is a $(C_6-C_{20})$fluorine-substituted aryl, a $(C_6-C_{20})$ fluorine-substituted aryloxy, or a $(C_1-C_{20})$fluorine-substituted alkoxy; and
$M^+$ is a metal inorganic cation or an organic cation.

15. The method of claim 12, wherein the anion containing compound has a structure:

$$M^+[SO_2Y]^-$$

wherein:
Y is a $(C_6-C_{20})$fluorine-substituted aryl, a $(C_6-C_{20})$ fluorine-substituted aryloxy, or a $(C_1-C_{20})$fluorine-substituted alkoxy; and
$M^+$ is a metal inorganic cation or an organic cation.

16. The method of claim 12, wherein the bidentate chelating ligand has the structure:

$$(R_1)(R_2)P-Z-P(R_1)(R_2)$$

wherein:
each $R_1$ and $R_2$ is independently chosen from a $(C_1-C_{50})$ alkyl group or a $(C_6-C_{50})$ aryl group; and
Z is a $(C_2-C_{50})$ alkylene group, a $(C_6-C_{50})$ arylene group, $-N(R_7)-$, $-P(R_7)-$, $-B(R_7)-$, or $-Si(R_7)_2-$ that links the two P atoms, where $R_7$ is a $(C_1-C_{50})$ alkyl group or a $(C_6-C_{50})$ aryl group.

* * * * *